(12) United States Patent
Sudo et al.

(10) Patent No.: US 11,197,609 B2
(45) Date of Patent: Dec. 14, 2021

(54) BIOLOGICAL INFORMATION ACQUIRING SYSTEM

(71) Applicant: NIHON KOHDEN CORPORATION, Tokyo (JP)

(72) Inventors: Kenta Sudo, Tokyo (JP); Yoshimoto Suzuki, Tokyo (JP); Takayuki Kaneko, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 724 days.

(21) Appl. No.: 15/525,497

(22) PCT Filed: Nov. 11, 2015

(86) PCT No.: PCT/JP2015/005633
§ 371 (c)(1),
(2) Date: May 9, 2017

(87) PCT Pub. No.: WO2016/075938
PCT Pub. Date: May 19, 2016

(65) Prior Publication Data
US 2017/0319064 A1    Nov. 9, 2017

(30) Foreign Application Priority Data
Nov. 11, 2014 (JP) .............................. JP2014-229038

(51) Int. Cl.
*A61B 5/00* (2006.01)
*H04N 7/18* (2006.01)
(Continued)

(52) U.S. Cl.
CPC ............ *A61B 5/002* (2013.01); *A61B 5/0006* (2013.01); *A61B 5/1113* (2013.01); *A61B 5/369* (2021.01);
(Continued)

(58) Field of Classification Search
CPC ...... A61B 5/0002–0031; A61B 5/0476; A61B 5/4094; A61B 5/1112–1115;
(Continued)

(56) References Cited

U.S. PATENT DOCUMENTS

2003/0088161 A1* 5/2003 Stengel .................. A61B 5/002
600/301
2004/0147818 A1* 7/2004 Levy .................. A61B 5/02055
600/300
(Continued)

FOREIGN PATENT DOCUMENTS

JP    2001-346768 A    12/2001
JP    2006-333013 A    12/2006
(Continued)

OTHER PUBLICATIONS

EPO Machine Translation of JP 2008047097 A. Retrieved May 22, 2019. (Year: 2019).*
(Continued)

*Primary Examiner* — Eric J Messersmith
(74) *Attorney, Agent, or Firm* — Pearne & Gordon LLP

(57) ABSTRACT

A biological signal acquirer is attached to a subject and acquires a biological signal of the subject. A transmitter carried by the subject transmits the biological signal. A first communication port and a first camera are installed in a first location and connectable to a network. A second communication port and a second camera are installed in a second location and connectable to the network. A biological information acquiring device is connectable to the network and
(Continued)

provided with a switcher. The switcher acquires, when communication establishment between the transmitter and the first communication port is detected, the biological signal through the first communication port as well as a first image taken by the first camera, and acquires, when communication establishment between the transmitter and the second communication port is detected, the biological signal through the second communication port as well as a second image taken by the second camera.

6 Claims, 3 Drawing Sheets

(51) Int. Cl.
*A61B 5/11* (2006.01)
*G16H 40/67* (2018.01)
*A61B 5/369* (2021.01)
*H04N 5/268* (2006.01)
*G16H 30/20* (2018.01)

(52) U.S. Cl.
CPC .......... *A61B 5/4094* (2013.01); *G16H 40/67* (2018.01); *H04N 5/268* (2013.01); *H04N 7/181* (2013.01); *A61B 2560/0431* (2013.01); *G16H 30/20* (2018.01)

(58) Field of Classification Search
CPC .......... A61B 5/1118; A61B 2560/0431; A61B 2560/0443; A61B 2560/045; A61B 2560/0462; A61B 2560/0468; H04N 5/222–268; H04N 7/18–188
See application file for complete search history.

(56) References Cited

U.S. PATENT DOCUMENTS

| | | | |
|---|---|---|---|
| 2004/0263353 A1* | 12/2004 | Imajo | A61B 5/0476 340/870.07 |
| 2006/0161072 A1* | 7/2006 | Mase | A61B 5/369 600/544 |
| 2012/0108917 A1* | 5/2012 | Libbus | A61B 5/1115 600/301 |
| 2012/0170474 A1* | 7/2012 | Pekarske | A61B 5/002 370/252 |
| 2014/0379369 A1* | 12/2014 | Kokovidis | A61B 5/002 705/2 |
| 2015/0206409 A1* | 7/2015 | Visvanathan | G08B 21/0423 340/573.1 |

FOREIGN PATENT DOCUMENTS

| | | | |
|---|---|---|---|
| JP | 2008-047097 A | | 2/2008 |
| JP | 2008047097 A | * | 2/2008 |
| JP | 2012-127561 A | | 7/2012 |
| JP | 2015-530890 A | | 10/2015 |

OTHER PUBLICATIONS

Japanese Office Action issued in Patent Application No. JP 2014-229038 dated Nov. 14, 2017.
International Search Report Issued in Patent Application No. PCT/JP2015/005633 dated Jan. 26, 2016.
Written Opinion Issued in Patent Application No. PCT/JP2015/005633 dated Jan. 26, 2016.

* cited by examiner

BIOLOGICAL INFORMATION ACQUIRING SYSTEM

TECHNICAL FIELD

The present invention relates to a system for acquiring biological information of a subject through a network installed in a facility.

BACKGROUND ART

For example, Patent Document 1 discloses a system of this kind. In the system, a biological signal of a subject, and an image taken from the subject are transmitted to a biological signal acquiring device through a network. The biological signal acquiring device is located remotely from the subject, and used by a medical person.

CITATION LIST

Patent Literature

PTL 1: Japanese Patent Publication No. 2001-346768 A

SUMMARY OF INVENTION

Technical Problem

It is an object of the invention to reduce burdens on both a subject and a medical person in the case where a biological signal and image of the subject must be acquired for a long period of time.

Solution to Problem

In order to achieve the above object, one aspect that the invention can take is a biological information acquiring system configured to acquire biological information of a subject through a network installed in a facility, the biological information acquiring system comprising:

a biological signal acquirer configured to be attached to the subject, and to acquire a biological signal of the subject;

a transmitter configured to be carried by the subject and to transmit the biological signal;

a first communication port configured to be installed in a first location in the facility and to be connectable to the network;

a first camera configured to be installed in the first location and to be connectable to the network;

a second communication port configured to be installed in a second location in the facility and to be connectable to the network;

a second camera configured to be installed in the second location and to be connectable to the network and;

a biological information acquiring device configured to be connectable to the network and comprising a switcher, wherein the switcher is configured to acquire, when communication establishment between the transmitter and the first communication port is detected, the biological signal through the first communication port as well as a first image taken by the first camera, and to acquire, when communication establishment between the transmitter and the second communication port is detected, the biological signal through the second communication port as well as a second image taken by the second camera.

According to the thus configured biological information acquiring system, the subject is allowed to move between the first location and the second location. In the case where the biological signal and image of the subject must be acquired for a long period of time, it is not necessary to constrain the subject to the front of a camera which is installed in a specific location. Therefore, a burden on the subject can be reduced.

When, in the first location, the subject connects the transmitter to the first communication port, the image acquisition source is switched over by the switcher of the biological signal acquiring device so that the first image containing the subject is acquired from the first camera installed in the first location. When, in the second location, the subject connects the transmitter to the second communication port, the image acquisition source is switched over by the switcher of the biological signal acquiring device so that the second image containing the subject is acquired from the second camera installed in the second location. Accordingly, in response to communication establishment which is performed by the subject, and which is between the transmitter and the first communication port or the second communication port, the first image of the first location or the second image of the second location where the subject resides can be acquired from the first camera or the second camera. While the subject is allowed to move, consequently, the necessity of the intervention of the medical person can be reduced, and a burden on the medical person can be reduced.

In the case where a biological signal and image of the subject must be acquired for a long period of time, therefore, burdens on both the subject and the medical person can be reduced.

DESCRIPTION OF EMBODIMENTS

Figure 1:
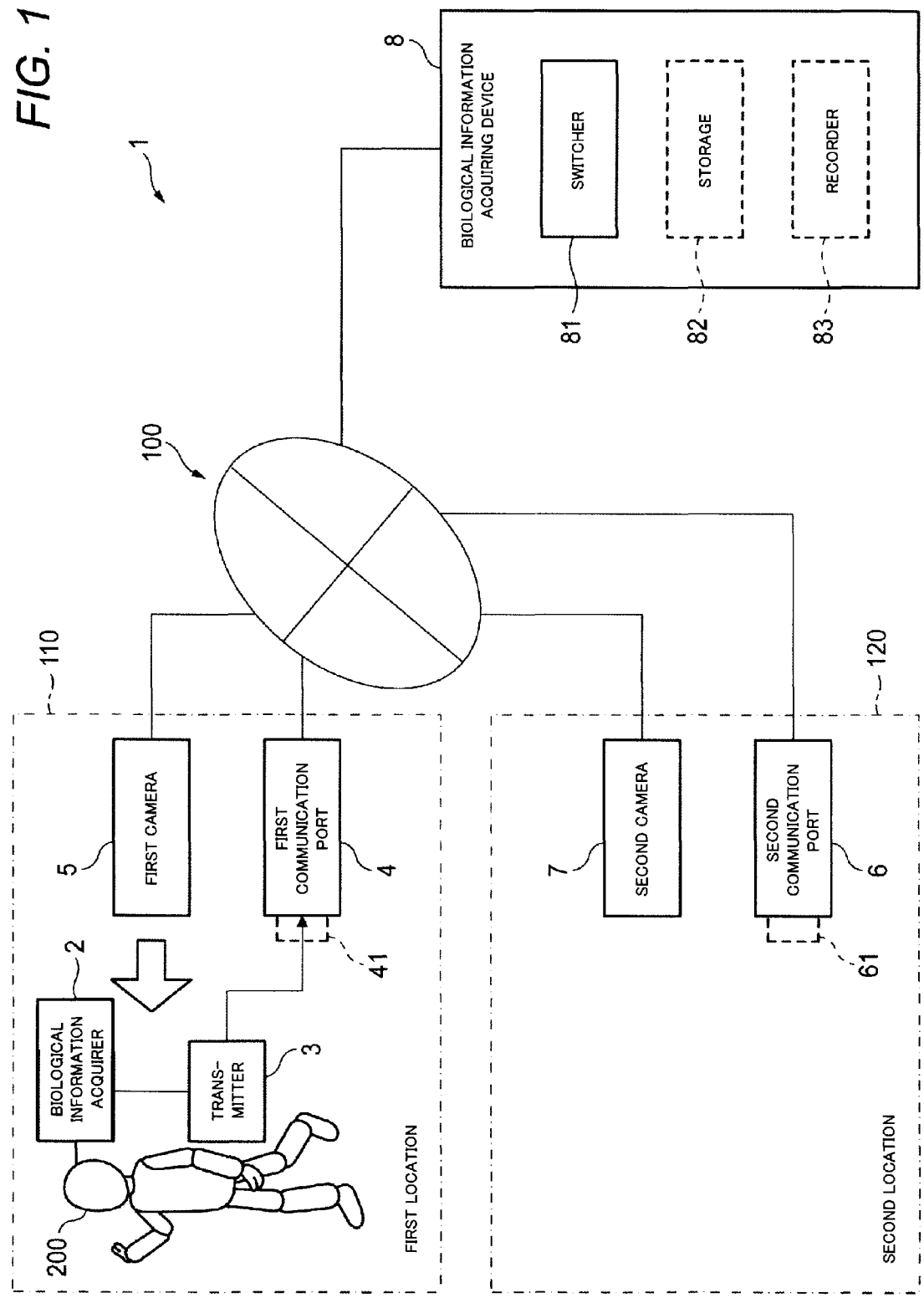
FIG. 1 is a view showing one state of a biological information acquiring system according to one embodiment.

Example embodiments will be described in detail with reference to the accompanying drawings. FIG. 1 is a functional block diagram showing a biological information acquiring system 1 according to one embodiment.

The biological information acquiring system 1 is a system which acquires biological information of a subject 200 through a network 100 installed in a facility. The network 100 is a network which is classified as, for example, a local area network. The term "facility" means not always a single building but also a facility configured by a plurality of buildings which are connected to one another through a local area network.

The biological information acquiring system 1 includes a biological signal acquirer 2. The biological signal acquirer 2 is configured so that it can be attached to a subject 200, and can acquire a biological signal of the subject 200. The biological signal acquirer 2 is configured by, for example, a plurality of electrodes which are to be attached to the head of the subject 200. The biological signal is, for example, brain waves.

The biological information acquiring system 1 includes a transmitter 3. The transmitter 3 is a device which is configured so as to be portably carried by the subject 200. Namely, the biological signal acquirer 2 and the transmitter 3 are moved together with the subject 200. The transmitter 3 is configured so that it can transmit a biological signal acquired by the biological signal acquirer 2. That is, the biological signal acquirer 2 and the transmitter 3 are configured to be able to perform wired or wireless communication.

Figure 2:
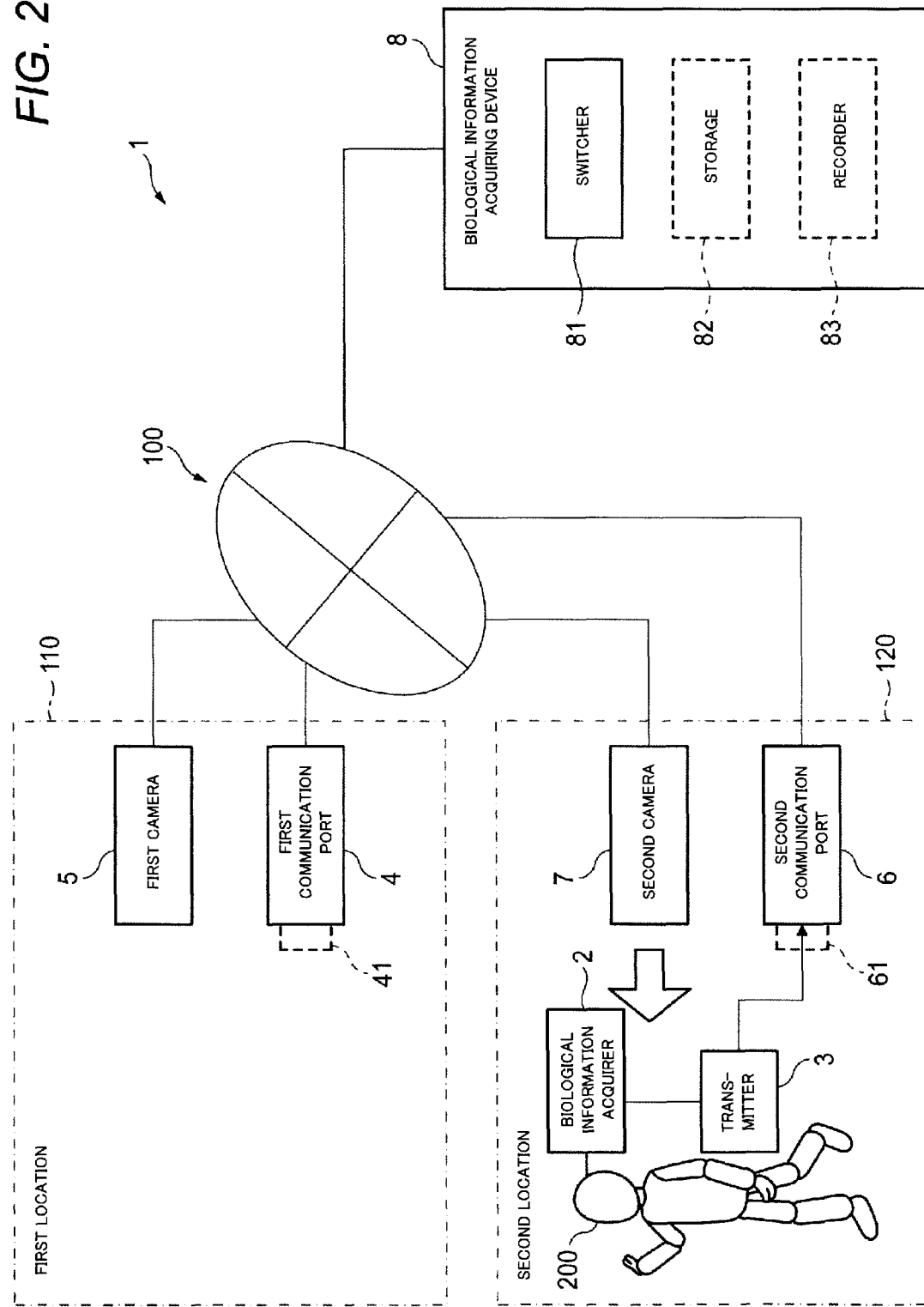
FIG. 2 is a view showing another state of the system.

The facility in which the network 100 is installed includes a first location 110 and a second location 120. For example, the first location 110 and the second location 120 are independent rooms which are in the facility. FIG. 1 shows a state where the subject 200 is in the first location 110. FIG. 2 shows a state where the subject 200 is in the second location 120.

The biological information acquiring system 1 includes a first communication port 4. The first communication port 4 is configured so as to be installable in the first location 110. The first communication port 4 is configured so as to be connectable to the network 100. The first communication port 4 is configured so as to be communicable with the transmitter 3. The first communication port 4 is configured so that, when communication between the transmitter 3 and the first communication port 4 is established, the first communication port 4 can relay the biological signal transmitted from the transmitter 3, to the network 100.

The biological information acquiring system 1 includes a first camera 5. The first camera 5 is configured so as to be installable in the first location 110. The first camera 5 is configured so as to be connectable to the network 100. The first camera 5 is configured so that it can take an image (first image) of the first location 110. The first camera 5 is configured so that it can transmit the taken first image as a first image signal to the network 100. The imaging range of the first camera 5 is set so that the subject 200 is contained in the first image in a state where the communication between the transmitter 3 and the first communication port 4 is established.

The biological information acquiring system 1 includes a second communication port 6. The second communication port 6 is configured so as to be installable in the second location 120. The second communication port 6 is configured so as to be connectable to the network 100. The second communication port 6 is configured so as to be communicable with the transmitter 3. The second communication port 6 is configured so that, when communication between the transmitter 3 and the second communication port 6 is established, the second communication port 6 can relay the biological signal transmitted from the transmitter 3, to the network 100.

The biological information acquiring system 1 includes a second camera 7. The second camera 7 is configured so as to be installable in the second location 120. The second camera 7 is configured so as to be connectable to the network 100. The second camera 7 is configured so that it can take an image (second image) of the second location 120. The second camera 7 is configured so that it can transmit the taken second image to the network 100. The imaging range of the second camera 7 is set so that the subject 200 is contained in the second image in a state where the communication between the transmitter 3 and the second communication port 6 is established.

The biological information acquiring system 1 includes a biological signal acquiring device 8. For example, the biological signal acquiring device 8 is an electroencephalograph. The biological signal acquiring device 8 is configured so as to be connectable to the network 100. The biological signal acquiring device 8 is located in a location which is remote from at least one of the first location 110 and the second location 120.

The biological signal acquiring device 8 includes a switcher 81. The switcher 81 is configured so as to, when communication establishment between the transmitter 3 and the first communication port 4 is detected, acquire the biological signal of the subject 200 from the first communication port 4 through the network 100, as well as the first image from the first camera 5. Furthermore, the switcher 81 is configured so as to, when communication establishment between the transmitter 3 and the second communication port 6 is detected, acquire the biological signal of the subject 200 from the second communication port 6 through the network 100, as well as the second image from the second camera 7.

Figure 3:
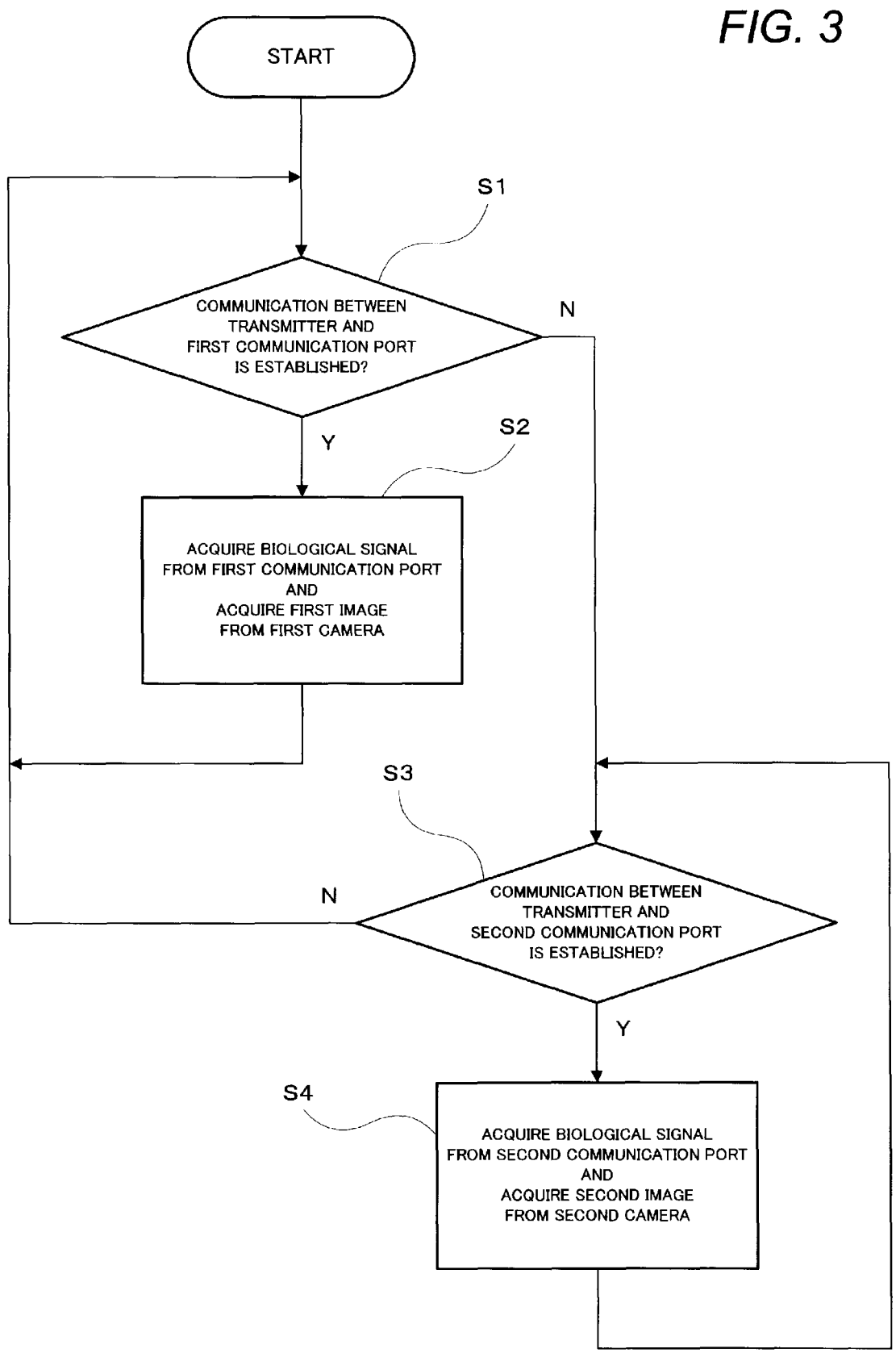
FIG. 3 is a chart showing a flow of operations of a biological information acquiring device included in the system.

FIG. 3 specifically shows the flow of a process which is executed by the switcher 81.

Firstly, the switcher 81 determines whether communication between the transmitter 3 and the first communication port 4 is established or not (step S1). When, as shown in FIG. 1, the subject 200 is in the first location 110, and the transmitter 3 is connected to the first communication port 4, communication between the transmitter 3 and the first communication port 4 is established. In this case (Y in step S1), the switcher 81 acquires the biological signal of the subject 200 from the first communication port 4 through the network 100, and the first image from the first camera 5 (step S2). Thereafter, the process returns to step S1.

As far as the communication between the transmitter 3 and the first communication port 4 continues to be established, the processes of step S1 and step S2 are repeated. In the case where the transmitter 3 has not originally connected to the first communication port 4, or where the subject 200 has canceled connection between the transmitter 3 and the first communication port 4, the switcher 81 determines that communication between the transmitter 3 and the first communication port 4 is not established (N in step S1). In this case, the process proceeds to step S3.

Next, the switcher 81 determines whether communication between the transmitter 3 and the second communication port 6 is established or not (step S3). When, as shown in FIG. 2, the subject 200 is in the second location 120, and the transmitter 3 is connected to the second communication port 6, communication between the transmitter 3 and the second communication port 6 is established. In this case (Y in step S3), the switcher 81 acquires the biological signal of the subject 200 from the second communication port 6 through the network 100, and the second image from the second camera 7 (step S4). Thereafter, the process returns to step S3.

As far as the communication between the transmitter 3 and the second communication port 6 continues to be established, the processes of step S3 and step S4 are repeated. In the case where the transmitter 3 has not yet connected to the second communication port 6, or where the subject 200 has canceled connection between the transmitter 3 and the second communication port 6, the switcher 81 determines that communication between the transmitter 3 and the second communication port 6 is not established (N in step S3). In this case, the process returns to step S1.

According to the thus configured biological information acquiring system 1, the subject 200 is allowed to move between the first location 110 and the second location 120. In the case where the biological signal and image of the subject 200 must be acquired for a long period of time, it is not necessary to constrain the subject 200 to the front of a camera which is installed in a specific location. Therefore, a burden on the subject can be reduced.

When, in the first location 110, the subject 200 connects the transmitter 3 to the first communication port 4 the image acquisition source is switched over by the switcher 81 of the biological signal acquiring device 8 so that the first image containing the subject 200 is acquired from the first camera 5 installed in the first location 110. When, in the second location 120, the subject 200 connects the transmitter 3 to the second communication port 6, the image acquisition source is switched over by the switcher 81 of the biological signal acquiring device 8 so that the second image containing the subject 200 is acquired from the second camera 7 installed in the second location 120. Accordingly, in response to communication establishment which is performed by the subject 200, and which is between the transmitter 3 and the first communication port 4 or the second communication port 6, the first image of the first location 110 or the second image of the second location 120 where the subject 200 resides can be acquired from the first camera 5 or the second camera 7. While the subject 200 is allowed to move, consequently, the necessity of the intervention of the medical person can be reduced, and a burden on the medical person can be reduced.

In the case where a biological signal and image of the subject must be acquired for a long period of time, therefore, burdens on both the subject and the medical person can be reduced.

As indicated by the dashed lines in FIGS. 1 and 2, the biological information acquiring system 1 includes a storage 82. In the case where the first communication port 4 is provided with a first network identifier in the network 100, and the second communication port 6 is provided with a second network identifier in the network 100, the storage 82 stores the first network identifier in advance in association with the first camera 5, and stores the second network identifier in advance in association with the second camera 7. The first network identifier and the second network identifier are enough to be specific identifiers. For example, IP addresses, MAC addresses, or the like which are different in the network 100 may be used.

According to the configuration, a network identifier which is to be used in identification of communication establishment can be used in the operation which is performed by the switcher 81 of the biological signal acquiring device 8, and which is performed for switching over the image acquisition source. Therefore, the switching operation can be easily automatized. In the case where a biological signal and image of the subject must be acquired for a long period of time, therefore, burdens on both the subject and the medical person can be further reduced.

The storage 82 stores the first network identifier in advance in association with first location information in the facility where the network 100 is installed. Moreover, the storage 82 stores the second network identifier in advance in association with second location information in the facility where the network 100 is installed. Examples of the first location information and the second location information are information indicating the physical positions of the first location 110 and the second location 120 in the facility, that indicating the kinds (the patient room of the subject 200, a rehabilitation space, and the like) of the rooms respectively corresponding to the first location 110 and the second location 120, etc.

As indicated by the dashed lines in FIGS. 1 and 2, the biological information acquiring system 1 includes a recorder 83. The recorder 83 is configured so as to record the biological signal of the subject 200 acquired from the first communication port 4, as well as the first image acquired from the first camera 5, in association with the first location information. Furthermore, the recorder 83 is configured so as to record the biological signal of the subject 200 acquired from the second communication port 6, as well as the second image acquired from the second camera 7, in association with the second location information.

According to the configuration, in addition to the biological signal and image of the subject 200, information indicating the location which is in the facility, and in which the subject 200 resides can be recorded. In the case where the biological signal and image of the subject must be acquired for a long period of time, therefore, not only burdens on both the subject and the medical person can be reduced, but also the acquired biological information can be analyzed in correlation to the location where the subject 200 resides.

The communication between the transmitter 3 and the first communication port 4 or the second communication port 6 may be performed through wireless communication or wired communication. In the case where the transmitter 3 is configured so as to be communicable with the first communication port 4 and the second communication port 6 via the wired communication, however, the subject 200 can visually check the connection between the transmitter 3 and the first communication port 4 or the second communication port 6. Furthermore, the communication between the transmitter 3 and the first communication port 4 or the second communication port 6 can be established by a simpler configuration. In the case where the biological signal and image of the subject must be acquired for a long period of time, therefore, not only burdens on both the subject and the medical person can be reduced, but also the configuration of the biological information acquiring system 1 can be simplified.

In this case, as indicated by the dashed line in FIG. 1, the transmitter 3 and the first communication port 4 are wire-connected to each other through a connector 41. As indicated by the dashed line in FIG. 2, moreover, the transmitter 3 and the second communication port 6 are wire-connected to each other through a connector 61. The connector 41 and the connector 61 have an identical configuration.

Therefore, the subject 200 can connect together always in the same method the transmitter 3 and the first communication port 4 or the second communication port 6. Furthermore, specifications of the connectors can be commonalized, and hence the biological information acquiring system 1 can be constructed easily and economically. In the case where the biological signal and image of the subject must be acquired for a long period of time, therefore, not only burdens on both the subject and the medical person can be further reduced, but also the configuration of the biological information acquiring system 1 can be further simplified.

The foregoing description of the embodiment has been made in order to facilitate understanding of the invention, and is not intended to limit the invention. It is a matter of course that the invention may be changed or improved without departing the spirit thereof, and includes equivalents thereof.

In the above embodiment, the case where the biological signal acquirer 2 acquires the brain waves, and the biological signal acquiring device 8 is an electroencephalograph has been described. In the case of an epilepsy patient, particularly, the brain waves and the image must be observed for a long period of time. According to the configuration of the embodiment, therefore, burdens on both an epilepsy patient and the medical person can be further reduced. However, the invention can be applied to an arbitrary biological signal which is requested to be acquired simultaneously with an image of the subject.

In the above embodiment, the storage 82 of the biological signal acquiring device 8 stores in advance the first network identifier of the first communication port 4 in association with the first camera 5, and stores in advance the second network identifier of the second communication port 6 in association with the second camera 7. The switcher 81 of the biological signal acquiring device 8 detects communication establishment between each communication port and the transmitter 3, by using the first network identifier and the second network identifier. However, the first communication port 4 and the second communication port 6 can be configured so as to transmit different signals to the network 100 when the communication is established. In this case, the storage 82 can be configured so as to store in advance the signal output from the first communication port 4 in association with the first camera 5, as well as output from the second communication port 6 in association with the second camera 7. The switcher 81 can be configured so as to switch over the image acquisition source based on the signal received by the biological signal acquiring device 8 and correspondence relationships stored in the storage 82.

In the above embodiment, the case where the subject 200 moves between the first location 110 and the second location 120 has been described. However, the number of locations to which the subject 200 moves is not limited to two. The subject 200 can freely move among three or more locations. In this case, the first location 110 and the second location 120 can be deemed as arbitrary two locations selected from the three or more locations.

In the above embodiment, the case where the first location 110 and the second location 120 are independent rooms has been described. However, the first location 110 and the second location 120 may be different locations in the same room. In this case, the first location 110 may be defined as an available range of the first camera 5, and the second location 120 may be defined as an available range of the second camera 7.

In the embodiment, the biological signal acquiring device 8 is located in a location which is in the facility where the network 100 is installed, and which is remote from the first location 110 and the second location 120. However, the biological signal acquiring device 8 may be located in a location which is remote from at least one of the first location 110 and the second location 120. Alternatively, the biological signal acquiring device 8 may be located in one of the first location 110 and the second location 120.

The present application is based on Japanese Patent Application No. 2014-229038 filed on Nov. 11, 2014, the contents of which are hereby incorporated by reference.

What is claimed is:

1. A biological information acquiring system configured to acquire biological information of a subject through a network installed in a facility, the biological information acquiring system comprising:
a biological signal acquirer configured to be attached to the subject, and to acquire a biological signal of the subject;
a transmitter configured to be carried by the subject and to transmit the biological signal;
a first communication port configured to be installed in a first location in the facility and to be connectable to the network;
a first camera configured to be installed in the first location, to be connectable to the network, and to take a first image when communication is established between the transmitter and the first communication port;
a second communication port configured to be installed in a second location in the facility and to be connectable to the network;
a second camera configured to be installed in the second location, to be connectable to the network, and to take a second image when communication is established between the transmitter and the second communication port; and
a biological information acquiring device configured to be connectable to the network and comprising a switcher,
wherein, in a case where the subject with the transmitter moves between the first location and the second location, the switcher is configured to:
determine whether communication between the transmitter and the first communication port is established or not;
acquire, in response to the communication establishment between the transmitter and the first communication port being determined, the biological signal through the first communication port as well as the first image taken by the first camera when the communication is established between the transmitter and the first communication port;
determine whether communication between the transmitter and the second communication port is established or not; and
acquire, in response to the communication establishment between the transmitter and the second communication port being determined, the biological signal through the second communication port as well as the second image taken by the second camera when the communication is established between the transmitter and the second communication port.

2. The biological information acquiring system as set forth in claim 1, wherein the biological information acquiring device comprises a storage configured to store in advance a first network identifier of the first communication port in association with the first camera, and to store in advance a second network identifier of the second communication port in association with the second camera.

3. The biological information acquiring system as set forth in claim 2,
wherein the storage is configured to store in advance the first network identifier in association with first location information, and to store in advance the second network identifier in association with the second location information; and
wherein the biological information acquiring system comprises a recorder configured to record the biological signal acquired from the first communication port as well as the first image acquired from the first camera in association with the first location information, and to record the biological signal acquired from the second communication port as well as the second image acquired from the second camera in association with the second location information.

4. The biological information acquiring system as set forth in claim 1, wherein the transmitter is configured to be wire-connectable with each of the first communication port and the second communication port.

5. The biological information acquiring system as set forth in claim 4, wherein a connector to be used for wire-connection between the transmitter and the first communication port and a connector to be used for wire-connection between the transmitter and the second communication port have an identical configuration.

6. The biological information acquiring system as set forth in claim 1,
   wherein the biological signal includes brain waves, and
   wherein the biological information acquiring device is an electroencephalograph.

\* \* \* \* \*